(12) United States Patent
Crnkovich et al.

(10) Patent No.: US 10,376,843 B2
(45) Date of Patent: Aug. 13, 2019

(54) METHOD OF DETECTING A LEAK IN A HEAT EXCHANGER OF A HEMODIALYSIS MACHINE

(71) Applicant: Fresenius Medical Care Holdings, Inc., Waltham, MA (US)

(72) Inventors: Martin Crnkovich, Walnut Creek, CA (US); Roland Levin, San Ramon, CA (US); Christopher McCormick, Walnut Creek, CA (US); Fei Wang, Concord, CA (US); Aiyuan Wang, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 254 days.

(21) Appl. No.: 15/411,610

(22) Filed: Jan. 20, 2017

(65) Prior Publication Data

US 2018/0207588 A1    Jul. 26, 2018

(51) Int. Cl.
*C02F 1/44* (2006.01)
*B01D 65/10* (2006.01)
(Continued)

(52) U.S. Cl.
CPC ......... *B01D 65/104* (2013.01); *A61M 1/169* (2013.01); *A61M 1/1629* (2014.02); *A61M 1/1662* (2014.02); *A61M 1/1668* (2014.02); *A61M 1/1688* (2014.02); *A61M 2205/15* (2013.01); *A61M 2205/18* (2013.01); *A61M 2205/3331* (2013.01); *A61M 2205/366* (2013.01); *A61M 2205/52* (2013.01); *A61M 2205/70* (2013.01);
(Continued)

(58) Field of Classification Search
USPC ........................................ 210/233, 646, 647
See application file for complete search history.

(56) References Cited

U.S. PATENT DOCUMENTS 8,409,441 B2   4/2013  Wilt
8,506,885 B2   8/2013  Kotsos et al.
(Continued)

FOREIGN PATENT DOCUMENTS

WO    2016184572 A1    11/2016

OTHER PUBLICATIONS

International Search Report and Written Opinion for application No. PCT/US2018/014495, dated May 29, 2018, 16 pages.

*Primary Examiner* — Hayden Brewster

(57) ABSTRACT

A leak may be detected in a heat exchanger of a hemodialysis device. A drain valve is opened by the controller, and then closed by the controller after a pre-selected time period. An initial pressure is determined in the spent dialysate circuit and stored in the memory. A system pressure is determined at periodic time intervals and compared to a pre-determined maximum pressure. The controller then determines whether the heat exchanger has a leak, in that in response to the system pressure exceeding a predetermined maximum pressure, a command is generated to execute an event including suspending a disinfectant operation with a disinfecting agent, and in response to the initial pressure subtracted from the system pressure being greater than a predetermined minimum pressure differential, a command is generated to execute an event including suspending the cleanse operation with the disinfecting agent.

12 Claims, 6 Drawing Sheets

(51) Int. Cl.
*A61M 1/16* (2006.01)
*B01D 11/00* (2006.01)
*B01D 61/00* (2006.01)

(52) U.S. Cl.
CPC ...... *B01D 2321/16* (2013.01); *B01D 2321/40* (2013.01)

(56) References Cited

U.S. PATENT DOCUMENTS

| | | | |
|---|---|---|---|
| 2002/0104800 A1* | 8/2002 | Collins | A61M 1/342 210/646 |
| 2003/0209475 A1 | 11/2003 | Connell et al. | |
| 2013/0126430 A1 | 5/2013 | Kenley et al. | |
| 2014/0174698 A1 | 6/2014 | Ritter et al. | |
| 2014/0319035 A1 | 10/2014 | Burbank et al. | |
| 2015/0314055 A1* | 11/2015 | Hogard | A61M 1/3649 210/137 |
| 2016/0356874 A1 | 12/2016 | Wang et al. | |

\* cited by examiner

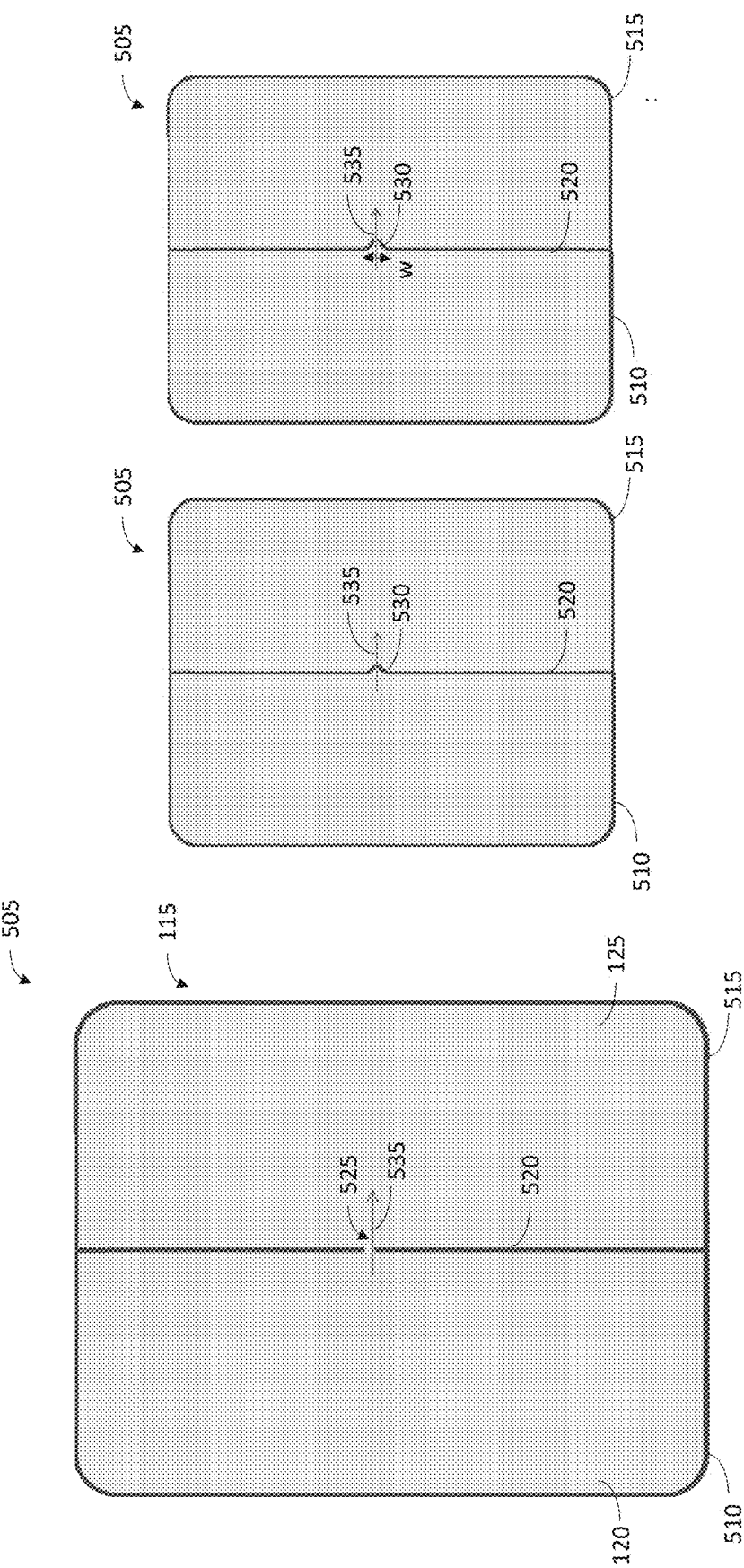

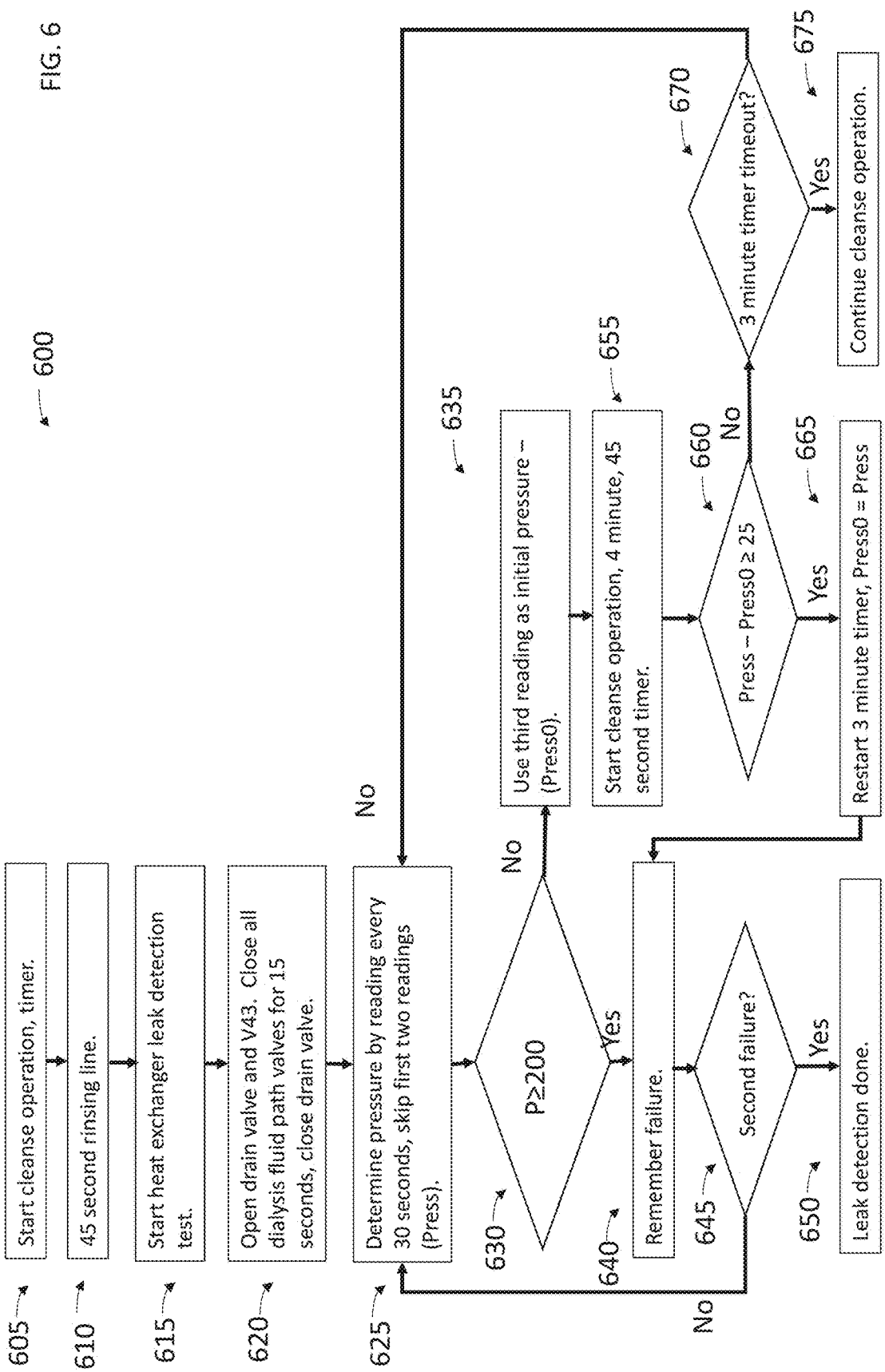

METHOD OF DETECTING A LEAK IN A HEAT EXCHANGER OF A HEMODIALYSIS MACHINE

FIELD OF THE DISCLOSURE

The disclosure generally relates to a controlled system and method for detecting a leak in a heat exchanger in a hemodialysis device, and more particularly to a controlled system and method for detecting a leak in a heat exchanger to prevent backflow contamination.

BACKGROUND OF THE INVENTION

Medical devices involving fluid flow typically involve a fluid flow path for a disinfectant operation such as a chemical disinfection. A hemodialysis device can function in place of a kidney by filtering waste, salt, and fluid from a patient's blood when the patient's kidneys do not function properly. To ensure the flow paths are properly cleaned for patient use, a chemical wash flows a disinfecting agent or other cleaning chemicals through the flow path. It is extremely critical that hemodialysis devices do not permit a chemical wash to contaminate a flow path containing fluid that may interact with a patient.

During a dialysis operation, a valve in a spent dialysate circuit is always closed, thereby preventing any potential contamination from a chemical wash. Additionally, an air-gap between a water inlet valve and a hydrochamber prevents any patient contamination if there is an external loss of water pressure. During a chemical wash operation, the valve is opened so that a chemical wash or other disinfectant flows from the spent dialysate side to the hydrochamber. A drain valve opens at a periodic time interval to disinfect the drain line, and fresh water flows through the water inlet valve to replace the volume emptied out the drain valve. Under normal circumstances, the fresh water circuit is under positive pressure, so water flows into the water inlet valve, and disinfectant is prevented from flowing back through the water inlet valve.

If an external water source fails, the water is no longer under positive pressure, and the chemical wash or disinfectant has a path for potential backflow. A heat exchanger may corrode over time, resulting in an opening in a wall or membrane. In the event of an external water source pressure failure, spent dialysate, which may include a disinfecting agent if a disinfectant operation is in process, may be drawn into the water circuit from the spent dialysate circuit, potentially contaminating the external water source and fluid that may interact with a patient. Although risk to the patient is remote, a solution is needed to detect leaks in a heat exchanger and prevent all potential backflow contamination to ensure patient safety.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In an embodiment, a method for detecting a leak in a heat exchanger of a hemodialysis device by a controller including a memory may comprise opening a drain valve by the controller, the drain valve being disposed in a spent dialysate circuit, and closing the drain valve by the controller after a pre-selected time period. The method may further include determining an initial pressure in the spent dialysate circuit by the controller, and storing the initial pressure in the memory, and sensing a system pressure at periodic time intervals and comparing to a pre-determined maximum pressure. The method may further include determining, by the controller, whether the heat exchanger has a leak, wherein: in response to the system pressure exceeding a predetermined maximum pressure, generating a command to execute an event including one or more of generating an alarm, suspending a disinfectant operation with a disinfecting agent, suspending system operation, and opening the drain valve, and in response to the initial pressure subtracted from the system pressure being greater than a predetermined minimum pressure differential, generating a command to execute an event including one or more of generating an alarm, suspending the disinfectant operation with the disinfecting agent, suspending system operation, and opening the drain valve.

In an embodiment, a non-transitory computer-readable medium storing an executable program by a controller for detecting a leak in a heat exchanger of a hemodialysis device may comprise opening a drain valve by the controller, the drain valve being disposed in a spent dialysate circuit and closing the drain valve by the controller after a pre-selected time period, determining an initial pressure in the spent dialysate circuit by the controller, and storing the initial pressure in the memory, sensing a system pressure at periodic time intervals and comparing to a pre-determined maximum pressure, and determining, by the controller, whether the heat exchanger has a leak, wherein: in response to the system pressure exceeding a predetermined maximum pressure, generating a command to execute an event including one or more of generating an alarm, suspending a disinfectant operation with a disinfecting agent, suspending system operation, and opening the drain valve; and in response to the initial pressure subtracted from the system pressure being greater than a predetermined minimum pressure differential, generating a command to execute an event including one or more of generating an alarm, suspending the disinfectant operation with the disinfecting agent, suspending system operation, and opening the drain valve.

BRIEF DESCRIPTION OF THE DRAWINGS

By way of example, specific embodiments of the disclosed device will now be described, with reference to the accompanying drawings, in which:

FIGS. 5A-5D illustrate an internal wall in a heat exchanger of a hemodialysis device according to an embodiment of the present invention;

FIG. 6 illustrates a flow diagram of a method of detecting a leak in a hemodialysis device according to an embodiment of the present invention.

DETAILED DESCRIPTION

Figure 1:
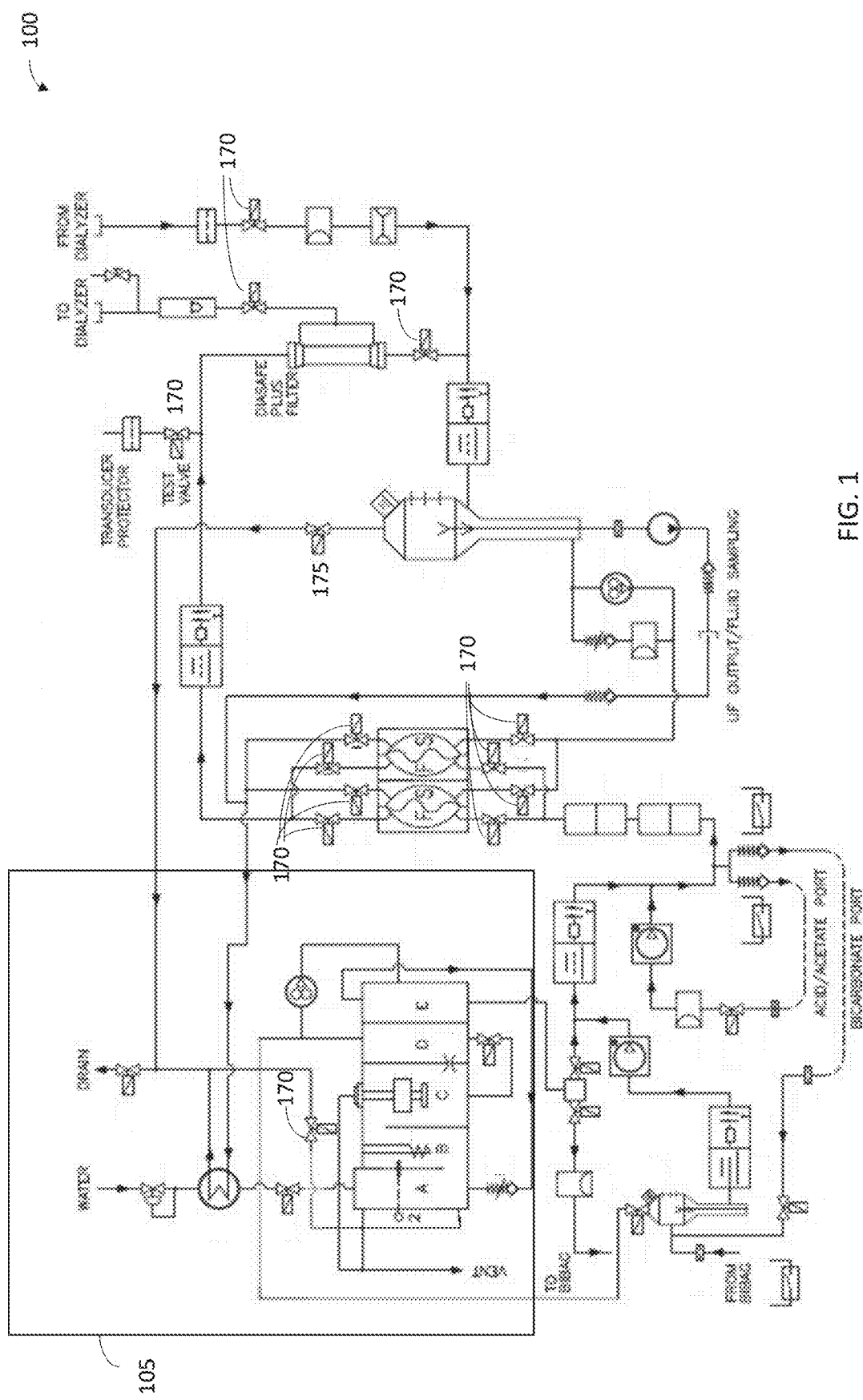
FIG. 1 illustrates a schematic diagram of a hemodialysis device according to an embodiment of the present invention.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Figure 2:
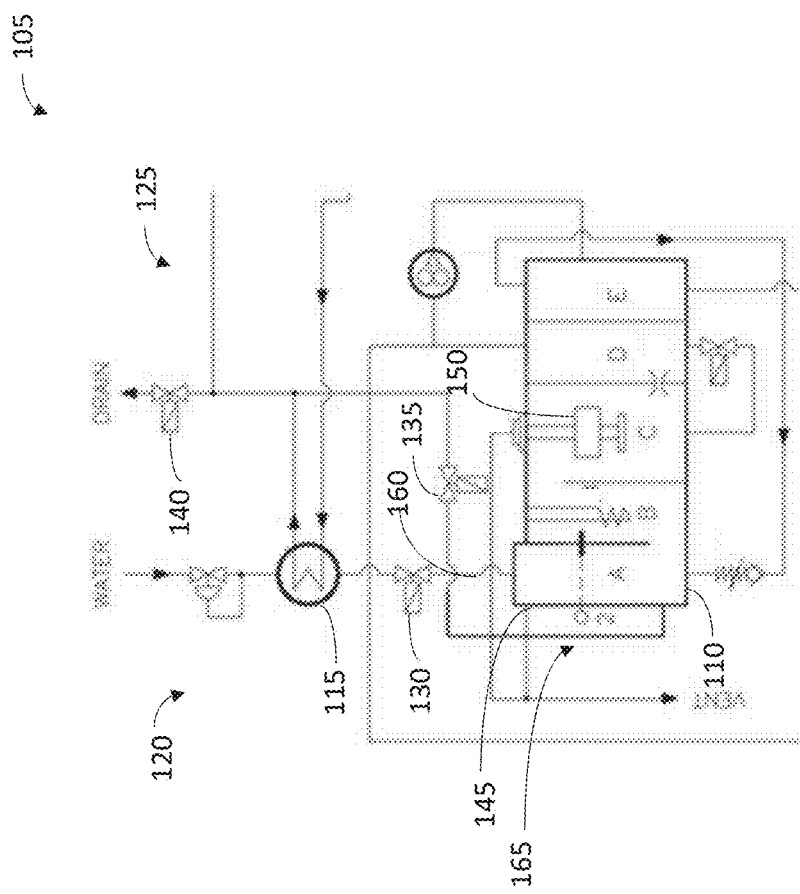
FIG. 2 illustrates a portion of the schematic diagram of FIG. 1 of a hemodialysis device according to an embodiment of the present invention.
Figure 4:
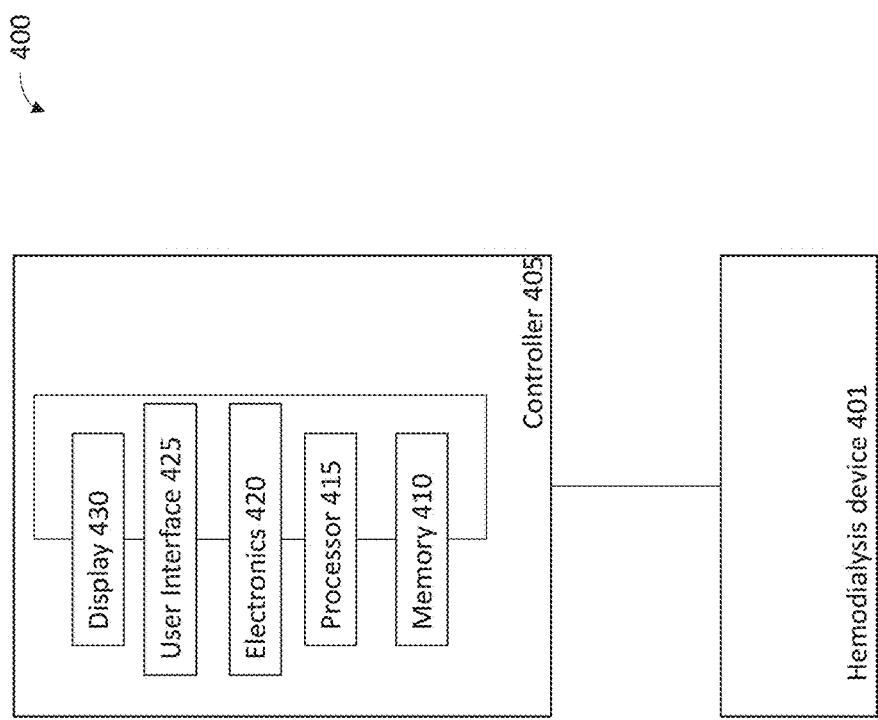
FIG. 4 illustrates a schematic of a controller and hemodialysis device according to an embodiment of the present invention.
Figure 3:
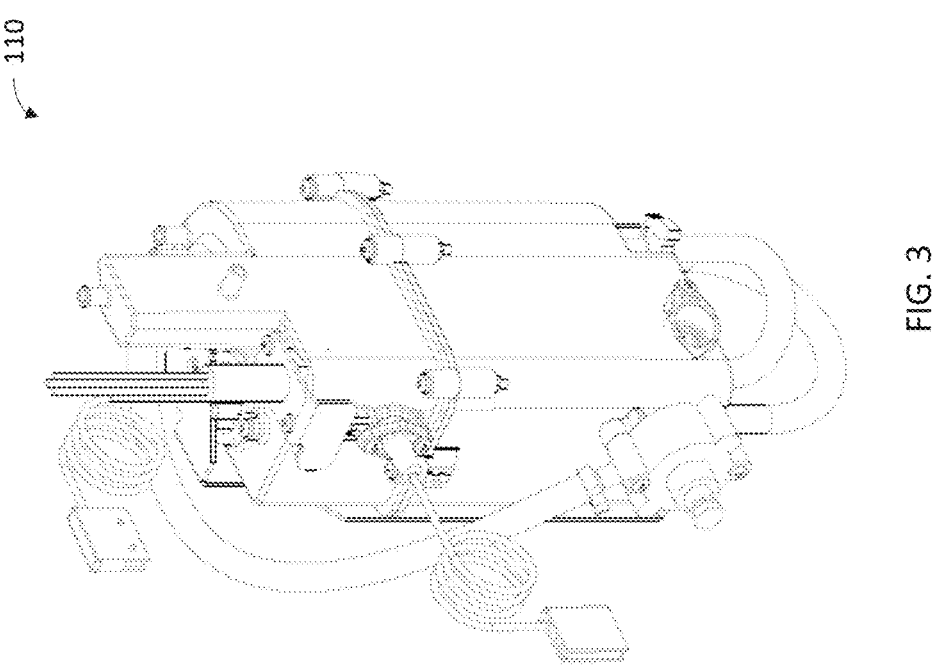
FIG. 3 illustrates a hydrochamber component of a hemodialysis device according to an embodiment of the present invention.
Figure 5D:
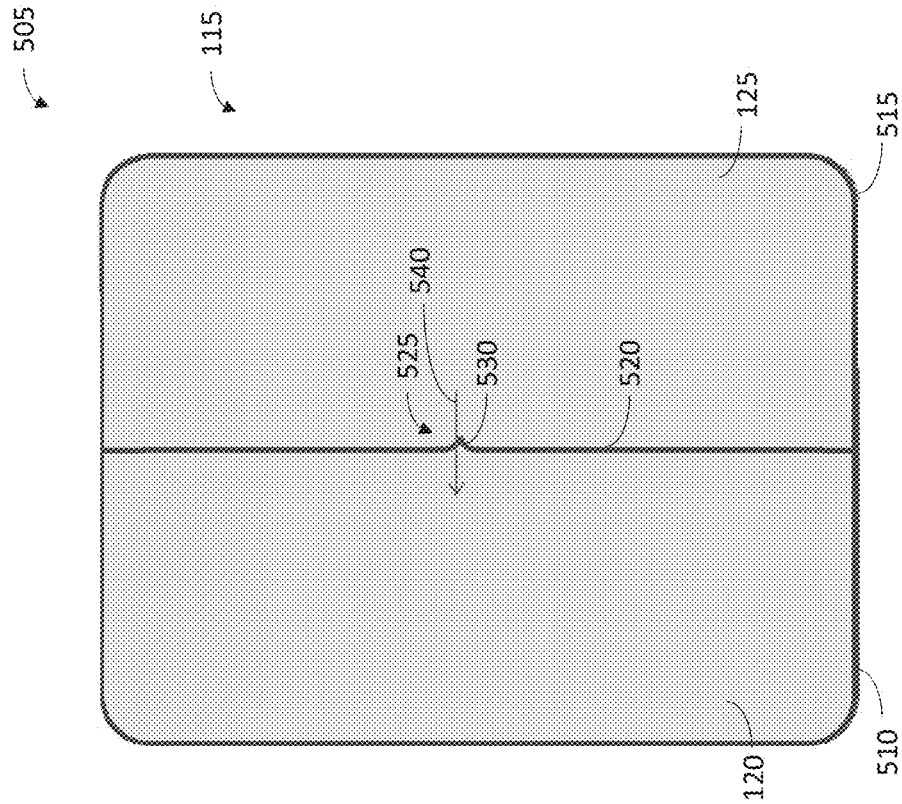

Referring to FIGS. 1 and 2, a schematic diagram of a hemodialysis device according to an embodiment of the present invention is shown. FIG. 2 shows a portion 105 of the schematic diagram 100 according to an embodiment of the present invention. Referring now to FIG. 3, a hydrochamber 110 of a hemodialysis device according to an embodiment of the present invention is shown. As described above, a hemodialysis device may include a fluid flow to a hydrochamber 110 from an external water source (not shown). FIG. 4 illustrates a schematic diagram 400 of a controller 405 for a hemodialysis device 401. The controller 405 may include a memory 410, a processor 415, one or more electronics 420, a user interface 425, and a display 430 operably connected to each other and connected to the hemodialysis device 401. In an embodiment, the hemodialysis device 401 may include one or more sensors (not shown) for measuring parameters of the hemodialysis device 401, including but not limited to fluid pressure(s), fluid temperature(s), and fluid volume.

The hemodialysis device 401 may include a hydrochamber 110 and a heat exchanger 115 in fluid communication with the hydrochamber 110. Referring back to FIGS. 1 and 2, a water circuit 120 and a spent dialysate circuit 125 in the hemodialysis device provide fluid flow in the portion 105 of the schematic diagram. An external water source (not shown) may provide fresh water to the water circuit 120. Water may flow through the heat exchanger 115 so that it is heated prior to entering the hydrochamber 110. A water inlet valve 130 may be disposed in the water circuit between the heat exchanger 115 and the hydrochamber 110. When the water inlet valve 130 is open, water may flow from the external water source into the hydrochamber 110. In embodiments, water may flow past an air gap 145 in the hydrochamber. The air gap 145 may prevent potential backflow of the water from the hydrochamber back through the water inlet valve 130.

The hydrochamber 110 may include a plurality of chambers 110A, 110B, 110C, 110D, and 110E. In an embodiment, water may enter a first chamber, e.g., chamber 110A and be heated in chamber 110B. Control of the water flow may occur in chamber 110C, for example, by including sensors and/or switches to monitor fluid in the hydrochamber. The fluid may be de-gassed or de-aerated in another chamber, e.g., 110D and/or 110E, so that balancing errors in the fluid are reduced. The fluid circuit is connected between the water inlet valve 130, a recirculation valve 135, and the hydrochamber 110.

Referring now to FIG. 2, a portion 105 of a schematic diagram of a hemodialysis device according to an embodiment of the present invention is shown. A recirculation valve 135 may be directly connected to the hydrochamber 110 so that a fluid flow path between the water inlet valve 130 and the recirculation valve 135 are independent of each other. For example, in an embodiment, a fluid flow path 160 may be between the water inlet valve 130 and the hydrochamber 110, and another, separate, fluid flow path 165 may be between the recirculation valve 135 and the hydrochamber 110.

As described above, during a dialysis operation or dialysis mode, backflow of fluid may be prevented by the air gap between the water inlet valve 130 and the hydrochamber 110. Additionally, a recirculation valve 135 remains closed, so that the spent dialysate circuit 125 remains closed off from the water circuit 120. Potential patient contamination is thereby prevented should an external loss of water pressure occur. In an embodiment, water may flow from an external water source (not shown) through the heat exchanger 115, through the water inlet valve 130, and into the hydrochamber 110 past the air gap 145. When the recirculation valve 135 is closed, the water circuit 120 may be isolated from the spent dialysate circuit 125. To detect a loss of water pressure, as described above, one or more sensors 150 may be disposed in a chamber 110A-110E. In an embodiment, the sensor 150 may be a float to detect a fluid level in the hydrochamber 110. In response to a change in the fluid level in the hydrochamber 110, a controller of the hemodialysis device may output a warning, alarm, and/or automatic shut-down.

During a disinfectant operation, the recirculation valve 135 is opened to flow a disinfecting agent from the spent dialysate circuit 125 to the hydrochamber 110 through the fluid flow path 165. In an embodiment, the disinfectant operation may be a disinfection wash and/or rinse. In an embodiment, the disinfecting agent may be a disinfectant. Periodic disinfection of the fluid circuits cleans the tubing in the system of microorganisms.

A drain valve 140 may be opened at periodic time intervals to drain fluid out of the spent dialysate circuit, so that the disinfecting agent disinfects the drain valve 140. To replace the drained fluid volume, the water inlet valve 130 opens to flow water in through the water circuit 120. The water circuit 120 is kept at a positive pressure over the spent dialysate circuit 125, so that water will always flow from a higher pressure area to the lower pressure hydrochamber when the water inlet valve 130 is opened. For example, the water pressure may be 20 psi. However, if an external water source fails, the fluid pressure may drop in the water circuit 120.

In the event of a loss of pressure at an external water source when the recirculation valve 135 is open during a disinfectant operation, the disinfecting agent is prevented from flowing through the water inlet valve 130 due to the air gap 145 and the independent fluid flow paths 160, 165. Thus, contamination is prevented and patient safety is ensured.

However, leaks may still occur at the heat exchanger 115, when fluid flows in the spent dialysate circuit 125 on a first side of the heat exchanger 115, and fluid flows in the water circuit 120 on a second side of the heat exchanger 115. The heat exchanger transfers heat between the fluid flow in the water circuit 120 and the fluid flow in the spent dialysate circuit 125. However, as described above, corrosive elements may also flow through the circuits 120, 125. Over time, a wall or membrane of the heat exchanger may corrode, resulting in a crack, tear, and/or opening. The opening may allow fluid to leak between circuits 120, 125.

As described above, it is critical to eliminate potential contamination of a flow path containing fluid that may interact with a patient. In the event of an opening developing in a wall, or membrane, of the heat exchanger, there is potential for leakage of fluid from a high pressure fluid flow path to a low pressure fluid flow path. As shown in FIGS. 5A-5D, a section view 505 of a heat exchanger 115 is illustrated. Water may flow through the water circuit 120 into the heat exchanger 115 on a first side 510, and spent dialysate and/or disinfecting agent may flow through the spent dialysate circuit 125 on a second side 515 of the heat exchanger 115. The two sides may be separated by a wall, or a membrane 520, so that heat may be transferred from fluid in the spent dialysate circuit to fluid in the water circuit, but the fluid flow paths remain isolated.

Over time, corrosive fluid may result in a crack, split, and/or hole forming an opening 525 in the membrane 520 of the heat exchanger 115 between the first side 510 and the second side 515. Fluid will thus flow from a higher pressure side (e.g., the first side 510 having the water circuit 120) of the heat exchanger 115 to a lower pressure side (e.g., the second side 515 having the spent dialysate circuit 125) of the heat exchanger 115, indicated by arrow 535. Under normal operating conditions, the water circuit 120 is at a positive pressure, so water may leak from the water circuit 120 to the spent dialysate circuit 125. The membrane 520 may be flexible or bendable, so that as fluid flows from a higher pressure area into a lower pressure area, edges 530 around the opening 525 may bend away from the area of high pressure, towards the spent dialysate circuit 125. Additionally, the higher pressure of the fluid flow may widen the opening 525 by pushing the edges 530 further away from the area of high pressure to increase the width w of the opening 525, resulting in an increase in the leak rate. As the spent dialysate fluid circuit 125 is drained from the hemodialysis device, a leak under these conditions poses no safety concern to the patient. However, this leak unnecessarily wastes water in the water circuit 120 and is preferably avoided.

In the event of a loss of pressure at an external water source (not shown), including if the loss occurs during a disinfectant operation, the fresh water circuit 120 is now at a negative pressure to the spent dialysate circuit 125. For example, with reference to FIG. 5D, if heat exchanger 115 includes an opening 525 in the membrane 520, fluid flows from an area of high pressure to an area of low pressure, or fluid from the spent dialysate circuit 125 could flow to the fresh water circuit 120 indicated by arrow 540 and contaminate the water circuit and/or external water source. If a pressure loss occurs during a disinfectant operation, a disinfecting agent flowing through the spent dialysate circuit 125, which may for example include bleach, may then flow into the water circuit 120 and/or external water source, resulting in contamination and a potential safety concern for patients. When an opening 525 is already formed with edges 530 bending towards the spent dialysate circuit 125, the higher pressure now being in the spent dialysate circuit 125 may close the edges 530 together somewhat to reduce and/or eliminate the width w of the opening 525 and thus reduce the leak, which does not necessarily eliminate the risk of contamination but could make the detection of a leak more difficult to discern. Therefore, it is important that any potential backflow leak in a low water inlet pressure event be mitigated as much as possible by being able to identify a leak through a sensitive detection test, such as described in an illustrated embodiment with flow diagram 600 shown in FIG. 6, prior to such an event occurring. It is advantageous to perform leak detection during a disinfectant operation as opposed to patient treatment operations because leak detection processes may interrupt operation of the hemodialysis device thereby increasing patient treatment times. Additionally, detecting a leak prior to a chemical rinse operation is more advantageous to ensure patient safety.

A leak may be detected by a hemodialysis device by executing a program from a controller stored in a memory. At step 605, the controller may generate a signal to start a disinfectant operation, such as a chemical rinse. The controller may also start a timer for monitoring the length of time allowed to detect a leak. For example, a specified period of time of 4 minutes may be set to ensure an existing leak will be detected. The period of time may be a function of the amount of fluid volume and/or length of tubing in the hemodialysis device, in that for a larger device, a longer time period may be necessary to ensure the tubing is properly cleaned. Similarly, in a smaller device having less tubing and/or length of tubing, a shorter time period may be needed to ensure the tubing is properly cleaned. Any period of time may be envisioned that is sufficient to allow for the program to be executed to detect for leaks within a given hemodialysis device setup.

At step 610, the rinse step of the disinfectant operation is run for a period of time. As described above, the controller may generate a signal to run the disinfectant operation, including the rinse step, for a time as a function of the device size requirements. For example, the rinse step of the disinfectant operation may be operated for 45 seconds.

At step 615, the controller generates a signal to start a leak detection test. At step 620, the controller generates a signal to open the drain valve 140 and valve 175. Valve 175 (designated as V43 in step 620 of FIG. 6) may be a venting valve opened during the leak detection test to connect the spent dialysate side of the heat exchange with a pressure sensor. As shown in FIG. 1, a plurality of valves 170 are disposed in the fluid circuit. When the drain valve 140 is opened, the valves 170 are closed for a period of time, and then the drain valve 140 is also closed. Steps 615 and 620 ensure the hemodialysis device has equalized pressure in the fluid circuits before beginning the leak test. This is advantageous to reduce and/or eliminate errors in detecting a leak.

At step 625, pressure readings at the spent dialysate side of the heat exchanger may be determined at periodic time intervals, for example, every 30 seconds. The controller may detect a pressure level, and the pressure level may be stored in a memory of the controller. At least the first two pressure readings may be discarded, to avoid potential error readings. At step 630, an initial pressure reading is compared to a pre-determined maximum pressure. In embodiments, the pre-determined maximum pressure may be 200 mm Hg. If the pressure reading is below the pre-determined maximum pressure, the pressure reading is stored in the memory as the initial pressure (Press0) at step 635. If the pressure reading exceeds the pre-determined maximum pressure, the pressure reading is stored in the memory of the controller as a failure at step 640.

At step 645, the failure is counted, so that if a second failure is recognized, that is, if a second system pressure reading exceeds the pre-determined maximum pressure, the leak detection test completes at 650, with the controller executing one or more of generating an alarm, suspending a disinfectant operation with a disinfecting agent, suspending system operation, and opening the drain valve. When the system pressure exceeds the predetermined maximum pressure, it is indicative of a massive leak being detected. If at step 645 the pressure failure stored is not a second failure, e.g., it is a first failure of exceeding the pre-determined maximum pressure, the system pressure readings at step 625 continue at the periodic time intervals. In embodiments, the leak detection program detects an increase of pressure. In response to the heat exchanger leaking, pressure from the fresh water circuit will cross the heat exchanger, thereby increasing pressure on the spent circuit side. As an alternative and/or in addition to a massive leak being detected at step 630, the program may be executed in steps to detect to smaller leaks.

Referring back to step 635, the initial pressure (Press0) is stored in the memory of the controller. At step 655, a timer for the leak test may be set. At step 660, the initial pressure is subtracted from the system pressure reading, Press—Press0. In response to the initial pressure subtracted from the system pressure being greater than a predetermined minimum pressure differential (e.g., a differential $\geq 25$), a failure occurs. When the initial pressure subtracted from the system pressure is greater than a predetermined minimum pressure differential, it is indicative of a small leak being detected. Step 665 resets the timer and the failure is stored back at step 640. Similar to steps 645 and 650, if the failure is a second failure, the controller may generate a command to execute an event including one or more of generating an alarm, suspending the disinfectant operation with the disinfecting agent, suspending system operation, and opening the drain valve. If the initial pressure subtracted from the system pressure is less than the predetermined minimum pressure, at step 670, the detection time is compared to a predetermined timer. If the timer is not exceeded, the process reverts to step 625. If the timer is exceeded, the disinfectant operation is continued at step 675 and the leak detection test is complete.

In an embodiment, a leak detection program may for example detect a leak rate as small in volume as 0.1 mL/min. In determining the desired acceptable leak rate, ANSI/AAMI RD62:2006 standards indicate a maximum allowable concentration of free chlorine of 0.5 mg/L parts per million (ppm). Generally, household bleach is about 6%, or 60,000 ppm. The hemodialysis device according to an embodiment of the present invention proportions one part bleach to 34 parts water, or 60,000 ppm divided by 35, equaling 1,714 ppm.

Thus, in order for the device to restrict to a maximum allowable concentration of 0.5 ppm, a reduction factor of 3,428 (e.g., 1714 ppm divided by 0.5 ppm) is needed. 0.1 mL/min*40 sec*1 min/60 sec=0.067 mL leakage. X mL/0.067 mL=3428→X=230 mL. For example, as long as at least 230 mL of water in the water circuit side is maintained, the chlorine concentration will not rise above the ANSFAAMI RD62:2006 standard of 0.5 ppm. In an embodiment of the hemodialysis device according to the present invention, a hydrochamber may hold more than three times the minimum water volume of 230 mL, e.g., approximately 740 mL, and may adequately detect leaks in the heat exchanger without putting a patient at risk.

As described above, leak detection in a heat exchanger is particularly critical to avoiding a worst case scenario when a pressure loss occurs at an external source of water, resulting in a negative pressure on the water circuit side, potentially drawing bleach or other harmful chemicals into a fluid circuit that may contaminate a patient or lead back to an external water source. An embodiment of the hemodialysis device may detect the loss of pressure at the external water source, e.g., within 40 seconds. In an embodiment, 40 seconds is determined as a function of the hemodialysis device described, as the time needed to determine a leak.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method for detecting a leak in a heat exchanger within a hemodialysis device, the hemodialysis device including one or more sensors for measuring fluid pressure, the hemodialysis device being communicatively coupled to a controller including a memory, the method comprising:

opening a drain valve within the hemodialysis device with the controller, the drain valve being disposed in a spent dialysate circuit;

closing the drain valve within the hemodialysis device with the controller after a pre-selected time period;

determining a first fluid pressure in the spent dialysate circuit with the one or more sensors in combination with the controller;

storing the first fluid pressure in the memory;

sensing additional fluid pressures at periodic time intervals;

determining, with the controller, whether the heat exchanger has a leak, by one or both of comparing each of the first fluid pressure and sensed additional fluid pressures at periodic intervals to a predetermined maximum fluid pressure, and comparing the first fluid pressure subtracted from each of the sensed additional fluid pressures at periodic time intervals to a predetermined minimum pressure differential;

wherein:

in response to one of the first fluid pressure or the sensed additional fluid pressures at periodic time intervals exceeding the predetermined maximum fluid pressure, generating a command to execute an event including one or more of generating an alarm, suspending a disinfectant operation with a disinfecting agent, suspending system operation, and opening the drain valve; and in response to the first fluid pressure subtracted from the sensed additional fluid pressures at periodic time intervals being greater than the predetermined minimum pressure differential, generating a command to execute an event including one or more of generating an alarm, suspending the disinfectant operation with the disinfecting agent, suspending system operation, and opening the drain valve.

2. The method according to claim 1, further comprising a plurality of valves, wherein after the opening the drain valve, the plurality of valves are closed to equalize subsequent fluid pressure in the hemodialysis device.

3. The method according to claim 1, wherein the preselected time period for closing the drain valve is stored in the memory.

4. The method according to claim 1, wherein the sensed additional fluid pressure is determined with the controller at 30 second time intervals.

5. The method according to claim 4, wherein the first fluid pressure is stored in the memory after the controller determines at least two initial fluid pressure readings.

6. The method according to claim 1, wherein the sensed additional fluid pressure at periodic time intervals is determined with the controller for a specified time period.

7. The method according to claim 1, wherein a massive leak is detected in response to at least one of the first fluid pressure or sensed additional fluid pressures at periodic time intervals exceeding the predetermined maximum pressure.

8. The method according to claim 1, wherein a small leak is detected in response to the first fluid pressure subtracted from the sensed additional fluid pressure at periodic time intervals being greater than the predetermined minimum pressure differential.

9. The method according to claim 1, wherein in response to a leak occurring in the heat exchanger, water from a fresh water circuit flows into the spent dialysate circuit such that subsequent fluid pressure on the spent dialysate circuit side is increased.

10. The method according to claim 9, wherein in response to detecting the leak in the heat exchanger, operation of the hemodialysis device is suspended such that spent dialysate and disinfecting agent, if the disinfectant operation is ongoing, is substantially prevented from flowing into the fresh water circuit.

11. The method according to claim 1, wherein leak detection is detected during a disinfectant operation.

12. The method according to claim 11, wherein the disinfectant operation is a chemical rinse using a disinfecting agent.

* * * * *